(12) United States Patent
Furuya et al.

(10) Patent No.: US 6,657,102 B2
(45) Date of Patent: Dec. 2, 2003

(54) ABSORBENT ARTICLE USING CONTINUOUS FILAMENTS AND ABSORBENT SHEET

(75) Inventors: Kodai Furuya, Kagawa (JP); Hiroo Hayashi, Kagawa (JP); Takamitsu Igaue, Kagawa (JP); Shinya Kaneko, Kagawa (JP)

(73) Assignee: Uni-Charm Corporation, Kawanoe (JP)

(*) Notice: Subject to any disclaimer, the term of this patent is extended or adjusted under 35 U.S.C. 154(b) by 84 days.

(21) Appl. No.: 09/935,405

(22) Filed: Aug. 23, 2001

(65) Prior Publication Data

US 2002/0029023 A1 Mar. 7, 2002

(30) Foreign Application Priority Data

Sep. 4, 2000 (JP) .......................... 2000-266761

(51) Int. Cl.[7] .................................. A61F 13/15
(52) U.S. Cl. ...................... 604/368; 604/383; 604/384
(58) Field of Search .................. 604/368, 378, 604/379, 383, 384

(56) References Cited

U.S. PATENT DOCUMENTS

| | | | | |
|---|---|---|---|---|
| 3,949,130 A | * | 4/1976 | Sabee et al. ............... | 428/192 |
| 5,492,751 A | * | 2/1996 | Butt et al. ................ | 428/198 |
| 5,695,487 A | * | 12/1997 | Cohen et al. .............. | 604/384 |
| 5,752,945 A | * | 5/1998 | Mosley et al. ............. | 604/370 |
| 5,972,505 A | * | 10/1999 | Phillips et al. ........... | 428/397 |
| 5,997,989 A | * | 12/1999 | Gessner et al. ............ | 428/152 |
| 6,093,870 A | * | 7/2000 | Carlsson .................. | 604/368 |
| 6,417,427 B1 | * | 7/2002 | Roxendal et al. ........... | 604/378 |
| 6,488,670 B1 | * | 12/2002 | Schild et al. ............. | 604/385.24 |

FOREIGN PATENT DOCUMENTS

| JP | 05-038350 | 2/1993 |
|---|---|---|
| JP | 09-156014 | 6/1997 |

* cited by examiner

*Primary Examiner*—Weilun Lo
*Assistant Examiner*—Jamisue A Webb
(74) *Attorney, Agent, or Firm*—Darby & Darby

(57) ABSTRACT

Disclosed is an absorbent article including: a liquid permeable surface layer formed of continuous filaments individually extending over the entire length of the surface layer, the continuous filaments including at least heat-fusible continuous filaments; a backing sheet; and a fibrous absorbent core located between the surface layer and the backing sheet and containing heat-fusible fibers. Between the surface layer and the fibrous absorbent core, disposed is an absorbent sheet which is formed of superabsorbent polymer to have a plurality of through passages. The surface layer and the fibrous absorbent core are partially fusion-bonded to each other via the through passages formed in the absorbent sheet for retaining the absorbent sheet between the surface layer and the fibrous absorbent core.

4 Claims, 4 Drawing Sheets

ABSORBENT ARTICLE USING CONTINUOUS FILAMENTS AND ABSORBENT SHEET

BACKGROUND OF THE INVENTION

1. Field of the Invention

The present invention relates to an absorbent article, such as a sanitary napkin, a disposable diaper and so forth, using a surface layer formed of continuous filaments and an absorbent sheet formed of superabsorbent polymer.

2. Description of the Related Art

An absorbent article, such as a sanitary napkin, a disposable diaper or the like, is provided with an absorbent layer between a liquid permeable surface sheet and a liquid impermeable backing sheet.

In order to make an absorbent article thin type with large liquid absorbing capacity, the absorbent layer is formed of a fibrous absorbent core and superabsorbent polymer (SAP). Conventionally, used is granular superabsorbent polymer, which is arranged on the surface of the fibrous absorbent core or contained in the fibrous absorbent core. When such granular superabsorbent polymer is used, it is required to uniformly disperse and retain the polymer without causing local concentration.

To this end, for example Japanese Unexamined Patent Publication No. Heisei 5-38350 discloses an absorbent core which is prepared by applying an adhesive in spots, lines or curved lines onto an absorbent material, dispersing granular superabsorbent polymer thereon, stacking another absorbent material thereon, and compressing the stack to be integrated.

On the other hand, in Japanese Unexamined Patent Publication No. Heisei 9-156014, there is disclosed an absorbent sheet of aggregate of fibers, in which granular superabsorbent polymer is bonded and retained on fibers within the absorbent sheet.

However, in both of the above-identified publications, since granular superabsorbent polymer is maintained within a fibrous absorbent core, the superabsorbent polymer is not always distributed uniformly in an absorbent layer to possibly cause local concentration. Therefore, the liquid absorbing performance is liable to fluctuate from place to place in the absorbent layer.

In the absorbent core disclosed in the Japanese Unexamined Patent Publication No. Heisei 5-38350, moreover, an adhesive is employed for fixing the granular superabsorbent polymer within the fibrous absorbent core. Since the adhesive is applied in spots, lines or curved lines, it is not possible to certainly fix all superabsorbent polymer. Furthermore, since the adhesive is remained within the fibrous absorbent core, such residual adhesive may possibly lower liquid permeability.

Next, in the absorbent sheet disclosed in Japanese Unexamined Patent Publication No. Heisei 9-156014, since the granular superabsorbent polymer is fusion-bonded on the fibers, there is a possibility that absorbing performance of the superabsorbent polymer may be lowered by fusion-bonding.

Furthermore, in the conventional absorbent article, a surface sheet, which is formed of a liquid permeable non-woven fabric or a synthetic resin film formed with a large number of openings, is provided on the fibrous absorbent core thus formed, and the fibrous absorbent core and the surface sheet are partially adhesive-bonded. Accordingly, adhesive-bonding process of the fibrous absorbent core and the surface sheet becomes necessary to increase process step. Furthermore, due to presence of an adhesive, liquid permeability of the surface sheet is degraded.

Moreover, the surface sheet thus formed of the liquid permeable non-woven fabric or the synthetic resin film having the openings causes the resistance as contacting with the skin of a wearer. That is, the conventional surface sheet does not provide good contact feeling.

SUMMARY OF THE INVENTION

The present invention has been worked out in view of the drawbacks set forth above. Therefore, it is an object of the present invention to provide an absorbent article in which superabsorbent polymer can be uniformly distributed and certainly fixed with respect to a fibrous absorbent core, which can eliminate necessity of use of adhesive which would otherwise lower liquid absorbing performance, and which can provide soft contact feeling to the skin of a wearer.

According to the present invention, there is provided an absorbent article comprising:

a liquid permeable surface layer formed of continuous filaments individually extending over the entire length of the surface layer, the continuous filaments including at least heat-fusible continuous filaments;

a backing sheet; and a fibrous absorbent core located between the surface layer and the backing sheet and containing heat-fusible fibers, wherein between the surface layer and the fibrous absorbent core, disposed is an absorbent sheet which is formed of superabsorbent polymer to have a plurality of through passages, and the surface layer and the fibrous absorbent core are partially fusion-bonded to each other via the through passages formed in the absorbent sheet for retaining the absorbent sheet between the surface layer and the fibrous absorbent core.

For example, the absorbent sheet may be formed with superabsorbent polymer fibers, and the surface layer and the fibrous absorbent core may be fusion-bonded via gaps defined between fibers of the absorbent sheet. Alternatively, the absorbent sheet may be a superabsorbent polymer film, and the surface layer and the fibrous absorbent core may be fusion-bonded via openings or cuts formed in the film.

Preferably, the heat-fusible continuous filaments in the surface layer and the heat-fusible fibers in the fibrous absorbent core are fusion-bonded at a plurality of fixing lines, which extend in a direction intersecting a direction along which the continuous filaments extend and are spaced apart from each other in the direction along which the continuous filaments extend.

In the present invention, the absorbent sheet formed of the superabsorbent polymer in the form of fibers or a film is firmly maintained between the surface layer and the fibrous absorbent core, so that the superabsorbent polymer is uniformly distributed in a liquid absorbing region. Here, no adhesive is required for maintaining the superabsorbent polymer. Therefore, the absorbent article can exhibit high liquid absorbing performance over a large area.

In addition, since the fibrous absorbent core and the surface layer are preliminarily integrated, the absorbent article can be simply manufactured.

Furthermore, since the surface layer is formed with the continuous filaments, it becomes so bulky as to have low density, to thereby provide soft contact feeling to the skin of a wearer. Especially since the continuous filaments extend over the entire length of the surface layer, no fiber end appears on the surface thereof to provide smooth feeling.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment of an absorbent article according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Figure 1:
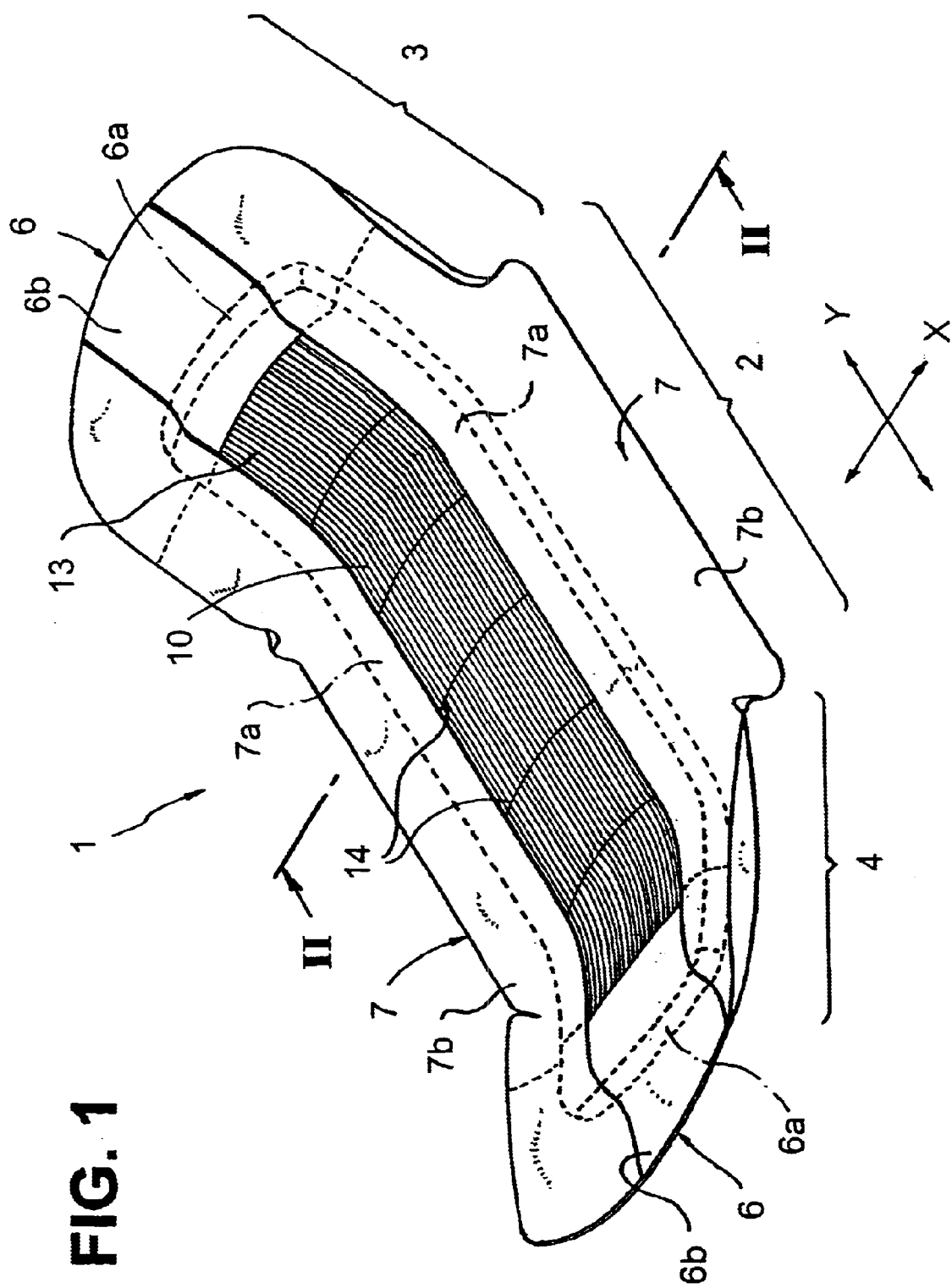
FIG. 1 is a perspective view of a sanitary napkin as an absorbent article according to one embodiment of the present invention, as viewed from a liquid receiving side.
Figure 2:
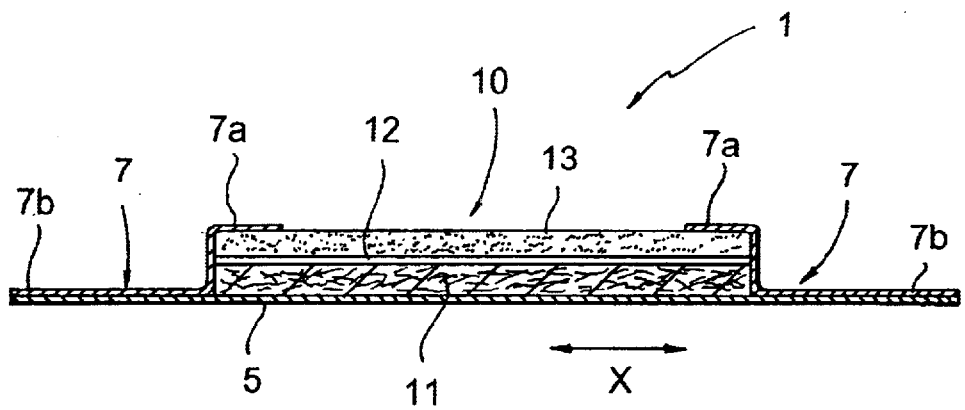
FIG. 2 is a section taken along line II—II of FIG. 1.
Figure 3:
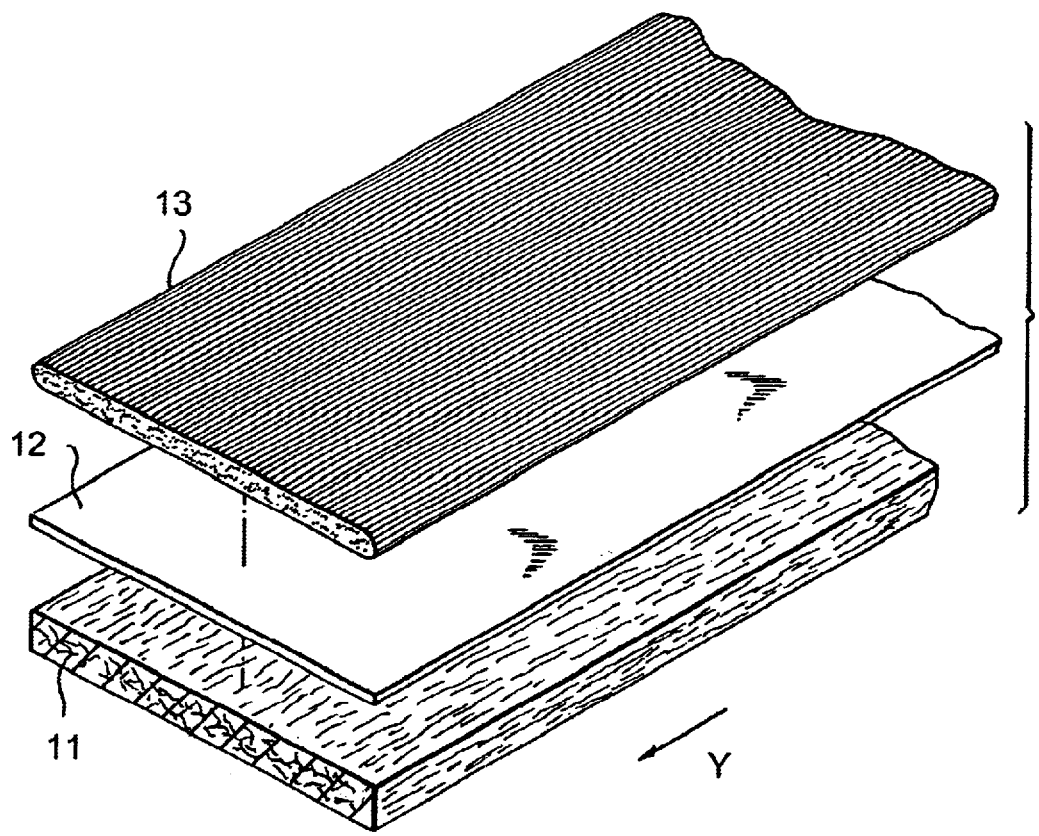
FIG. 3 is a perspective view for explaining a manufacturing process of a structural body.
Figure 4:
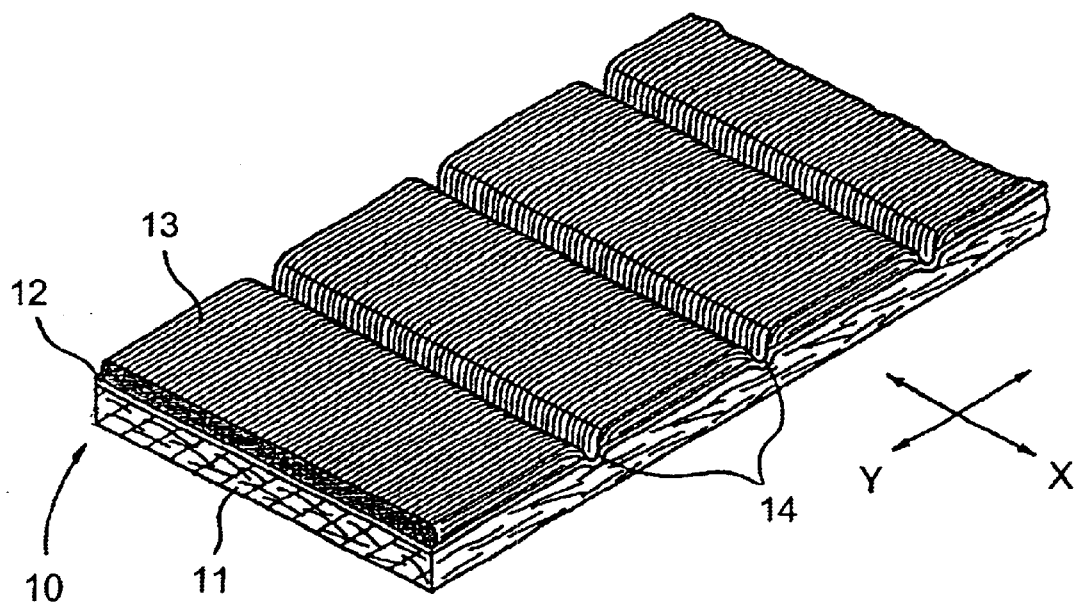
FIG. 4 is a perspective view showing an integrated structural body.
Figure 5:
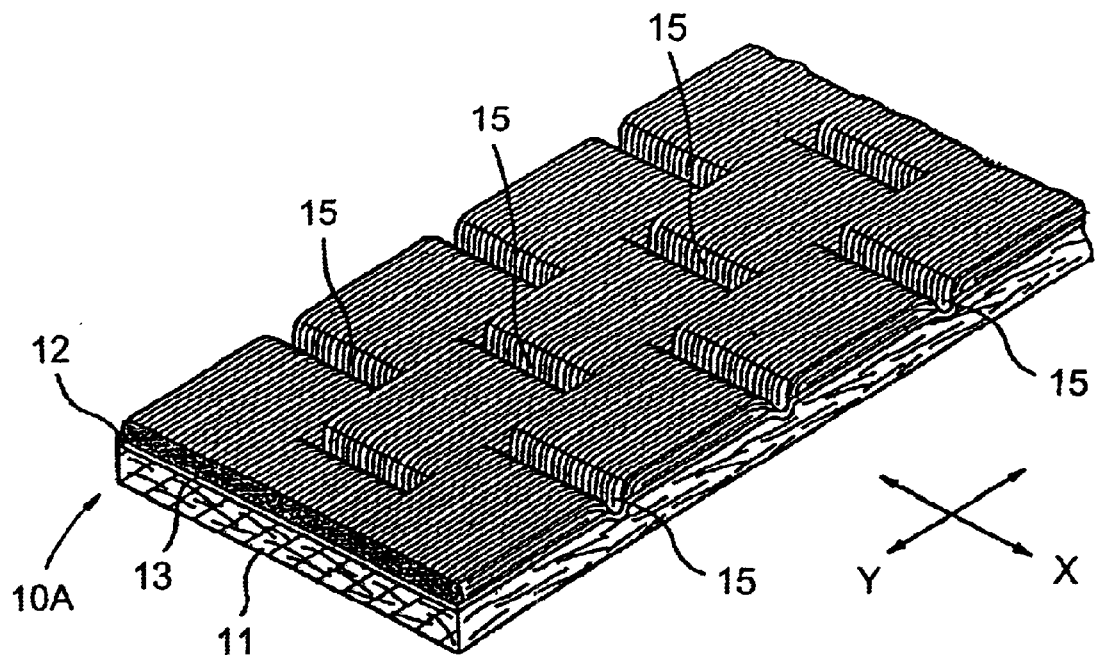
FIG. 5 is a perspective view showing a structural body of another construction.
Figure 6:
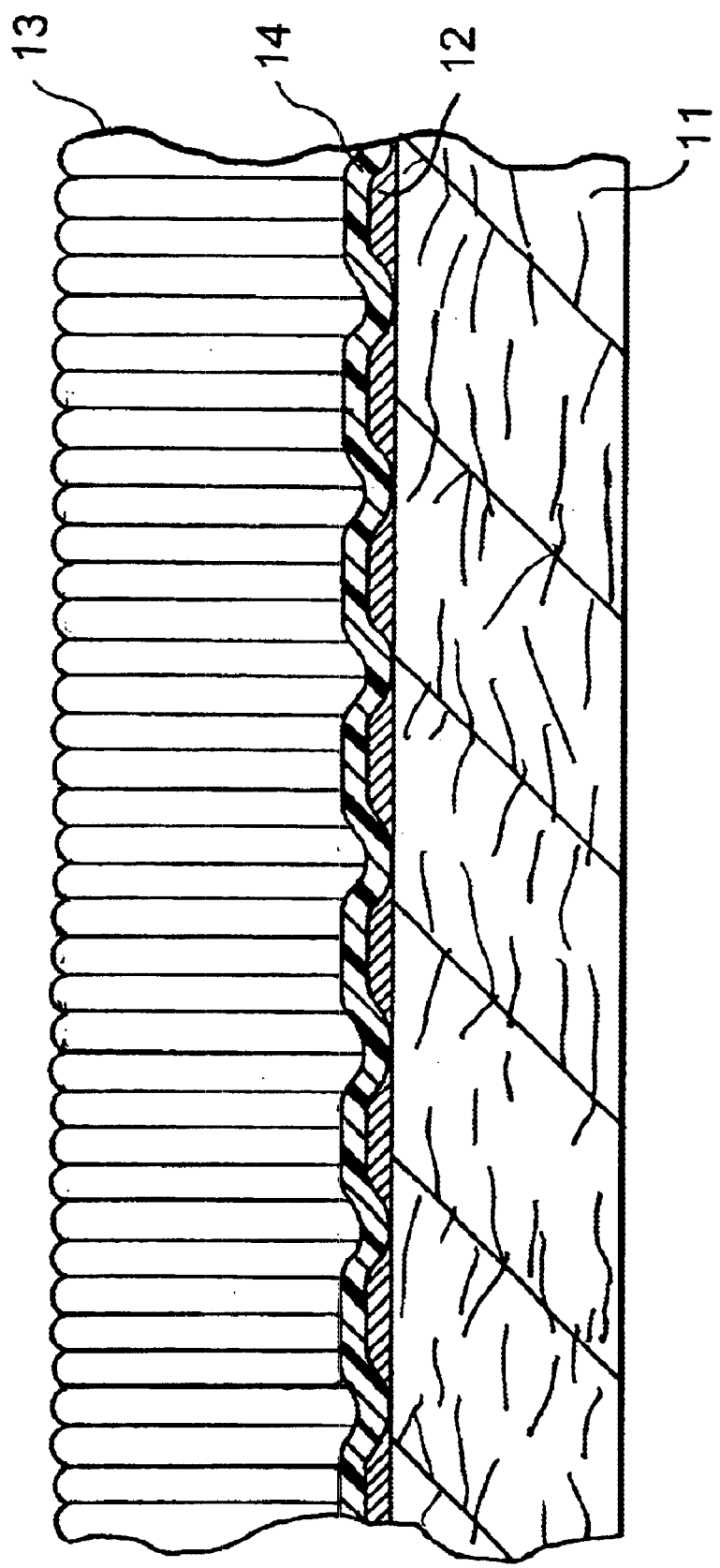
FIG. 6 is an enlarged section view taken along line II—II of FIG. 1.

FIG. 1 is a perspective view of a sanitary napkin as an absorbent article according to one embodiment of the present invention, as viewed from a liquid receiving side, FIG. 2 is a section taken along line II—II of FIG. 1, FIG. 3 is a perspective view for explaining a manufacturing process of a structural body, FIG. 4 is a perspective view showing an integrated structural body, FIG. 5 is a perspective view showing a structural body of another construction, and FIG. 6 is an enlarged section view taken along line II—II of FIG. 1 for illustration of through passages.

A sanitary napkin 1 shown in FIG. 1 has an intermediate portion 2, a front portion 3 and a rear portion 4. As shown in the section in FIG. 2, the sanitary napkin 1 has a structural body 10 formed by stacking and integrating a fibrous absorbent core 11, an absorbent sheet 12 and a surface layer 13. The structural body 10 is laid on a liquid impermeable backing sheet 5. As shown in FIG. 1, liquid impermeable end sheets 6 and 6 are provided on longitudinally opposite end portions of the sanitary napkin 1 (i.e., on an end portion on the side of the front portion 3 and on an end portion on the side of the rear portion 4), and liquid impermeable side sheets 7 and 7 are provided on laterally opposite side portions of the sanitary napkin 1 (i.e., on right and left side portions of the sanitary napkin 1). More specifically, each end sheet 6 is adhesive bonded to the surface of the structural body 10 at a portion indicated by 6a, and joined (bonded) to the backing sheet 5 at a remaining portion indicated by 6b. Also, each side sheet 7 is adhesive bonded to the surface of the structural body 10 at a portion indicated by 7a, and joined (bonded) to the backing sheet 5 at a remaining portion indicated by 7b. Thus, since front and rear end portions and left and right side portions of the surface of the structural body 10 are covered by the portions 6a of the end sheets 6 and the portions 7a of the side sheets 7, the structural body 10 is exposed on the liquid receiving side surface of the sanitary napkin 1 in a longitudinally elongated rectangular shape from a midway position of the front portion 3, through the intermediate portion 2, to a midway position of the rear portion 4.

The backing sheet 5 is liquid impermeable and is formed of a moisture permeable resin film, a non-woven fabric or a composite sheet, in which a resin film and a non-woven fabric are joined. The end sheets 6 and the side sheets 7 are formed of a non-woven fabric, such as through air bonded non-woven fabric, point bonded non-woven fabric, spun bonded non-woven fabric, spun laced non-woven fabric, melt blown non-woven fabric, air laid non-woven fabric and so forth. Preferably, the sheets 6 and 7 are hydrophobic or water repellent.

As shown in FIGS. 2 and 4, the fibrous absorbent core 11, the absorbent sheet 12 and the surface layer 13 of the structural body 10 are stacked and then integrated by partially fixing them at fixing lines 14. As will hereinafter be described in detail, the surface layer 13 is formed of continuous filaments each extending in a longitudinal direction (Y direction) of the sanitary napkin 1. The fixing lines 14 are spaced apart from each other in the longitudinal direction (Y direction) along which each continuous filaments of the surface layer 13 extends. In this embodiment, as shown in FIGS. 1 and 4, each fixing line 14 extends in straight completely across the structural body 10 in a width or lateral direction (X direction) perpendicular to the longitudinal direction (Y direction).

The fibrous absorbent core 11 is formed by blending hydrophilic fibers, such as pulp, rayon or the like, and heat-fusible synthetic fibers. These hydrophilic fibers and synthetic fibers may be uniformly dispersed within the fibrous absorbent core 11. Alternatively, the synthetic fibers may be unevenly distributed between upper and lower portions of the fibrous absorbent core 11 so as to contain greater amount of synthetic fibers in the upper portion (surface side portion) than that in the lower portion. Examples of the heat-fusible synthetic fibers include: conjugated synthetic fibers of core-sheath structure, such as those of PE/PET, PE/PP or the like, in which sheath portion is made of PE; side-by-side type conjugated synthetic fibers, such as those of PE/PET, PE/PP or the like; and mono fibers, such as those of PE, PP, PET or the like. The fibrous absorbent core 11 may be in a form of non-woven fabric, such as air laid non-woven fabric, or in a form of fibrous web.

On the fibrous absorbent core 11, the absorbent sheet 12 is stacked. The absorbent sheet 12 may be prepared such that fibers formed only of superabsorbent polymer or fibers containing superabsorbent polymer as primary component are formed into a sheet. The absorbent sheet 12 may be in a form of non-woven fabric or fibrous web.

The superabsorbent polymer may be a copolymer composed of polyacrylic acid type polymer, polyvinyl alcohol type polymer, maleic anhydride type polymer or the like as primary component, incorporating plastic monomer and crosslinking agent. For example, the superabsorbent polymer is formed into fibers such that a solution of copolymer containing homopolymer of neutralized substance of acrylic acid, acrylic ester as plastic monomer, and hexapropylene glycol monomethacrylate as crosslinking agent is extruded through a fine nozzle for spinning, and after spinning, heating is effected to cause crosslinking reaction.

Alternatively, the absorbent sheet 12 may be a film formed of the superabsorbent polymer. This film is formed with a large number of fine diameter openings (through holes) in uniformly distributed manner, or a large number of fine cuts in uniformly distributed manner.

When the superabsorbent polymer is used in the form of fibers for the absorbent sheet 12, gaps between the fibers may serve as through passages, as shown in FIG. 6. On the other hand, when the superabsorbent polymer is used in the form of film for the absorbent sheet 12, the openings or cuts may serve as through passages.

The surface layer 13 is a layer of continuous filaments. The individual continuous filaments extend in the longitudinal direction (Y direction) over the entire length of the structural body 10 without interruption. The surface layer 13 is prepared by opening a tow (i.e., a bundle of crimped continuous filaments). By opening process, the individual continuous filaments are loosened and separated from each other to provide uniform bulkiness in the width direction. The opened tow is stacked on the absorbent sheet 12.

The continuous filaments forming the surface layer 13 include at least continuous filaments formed of feat-fusible hydrophobic synthetic resin. Examples of the heat-fusible continuous filaments include: conjugated synthetic fibers of core-sheath structure, such as those of PE/PET, PE/PP or the like, in which sheath portion is made of PE; side-by-side type conjugated synthetic fibers, such as those of PE/PET, PE/PP or the like; and mono fibers, such as those of PE, PP, PET or the like. It is preferred that the continuous filaments contain inorganic filler for whitening, such as titanium oxide or the like, in the content of 0.5 to 10% by weight. By whitening process, menstrual blood or the like absorbed in the absorbent sheet 12 and the fibrous absorbent core 11 can be easily concealed from external view. The individual continuous filaments may have a circular or modified cross-section.

It is also preferred that the continuous filaments are treated to be hydrophilic by applying hydrophilic oil solution onto the filaments or by kneading hydrophilic oil solution in the resin for forming the filaments.

Crimping is provided for continuous filaments upon production by means of crimper, and number of crimp is increased by pre-heating calender or hot air treatment. In the alternative, through pre-heating calender, drawing and relaxing are repeated to cause strain in orientation of resin forming continuous filaments to cause crimp in coil form.

The tow of crimped continuous filaments is transported between transporting rolls. At this time, tension force is applied in the direction along which the filaments extend, and then the tension force is released. These processes are repeated to separate individual continuous filaments from each other for opening. In the alternative, it is also possible to perform opening of the tow by urging sliding plates onto the tow from opposite sides. In this method, the tow transported between transporting rolls is slidingly contacted with the sliding plates, and individual filaments are separated from each other by sliding contact force for opening. The latter method employing the sliding plates has been disclosed in commonly owned co-pending U.S. Patent Application for "METHOD AND APPARATUS FOR OPENING CONTINUOUS FILAMENTS" (claiming priority based on Japanese Patent Application No. 2000-265458). The disclosure of the above-identified commonly owned co-pending U.S. Patent Application is herein incorporated by reference. The layer of the continuous filaments thus opened from the tow has a small filament density and a large apparent width.

The continuous filaments of the surface layer 13 have a fineness in a range of 1.1 to 20 dtex, and preferably in a range of 1.1 to 11 dtex. In the individual continuous filaments, number of crimp is in a range of 5 to 30 per inch, and preferably in a range of 15 to 30, and crimp modulus of elasticity is preferably greater than or equal to 70%.

Number of crimp is based on JIS L-1015 and crimp modulus of elasticity is based on JIS L-1074. In case of the filament of a fineness less than 5.5 dtex, an initial load of 0.49 mN is applied in pulling direction, and in case of the filament of a fineness greater than or equal to 5.5 dtex, an initial load of 0.98 mN is applied in pulling direction. Number of crimp referred to is number of threads (peaks) per 1 inch (25 mm) when the initial load is applied.

On the other hand, the crimp modulus of elasticity is expressed by:

$$\{(b-c)/(b-a)\} \times 100 \ (\%)$$

wherein a is a length of filament when the initial load is applied, b is a length when the crimp is stretched by applying a tension force of 4.9 mN per 1.1 dtex for 30 seconds, and c is a length as applied the initial load again after 2 minutes from releasing the tension force.

The structural body 10 is manufactured in the following manner. First, as shown in FIG. 3, the fibrous absorbent core 11 of a given width, such as air laid non-woven fabric, is continuously fed in the longitudinal direction (Y direction) by transporting rolls. Onto the fibrous absorbent core 11, there is fed and stacked the absorbent sheet 12 having a width equal to or slightly larger than that of the fibrous absorbent core 11. Onto the absorbent sheet 12, moreover, there is fed and stacked the surface layer 13 which is spread (widened) to have substantially the same width as that of the fibrous absorbent core 11 and to have uniform bulkiness in the width direction.

Then, the fibrous absorbent core 11, the absorbent sheet 12 and the surface layer 13 thus stacked into three-layered structure are fed between a pair of rolls: one being a roll having smooth surface; the other being a welding roll having protrusions on the surface thereof. The protrusions extend in the axial direction of the roll (corresponding to the X direction) and are at a given pitch in the circumferential direction of the roll. At this time, the three-layered structure is fed between the paired rolls in such a manner that the fibrous absorbent core 11 is confronted by the smooth surface roll. While passing through the rolls, the three-layered structure is clamped by the protrusions to form the fixing lines 14. The welding roll is a heating roll or an anvil for sonic sealing.

By a clamping pressure and a heat applied to fibers, the heat-fusible fibers contained in the fibrous absorbent core 11 and the heat-fusible continuous filaments of the surface layer 13 are melted to be fusion-bonded to each other via the through passages which are distributed in the absorbent sheet 12 in large numbers. Specifically, when the absorbent sheet 12 is formed with the superabsorbent polymer fibers, the heat-fusible fibers and the heat-fusible continuous filaments are fusion-bonded to each other via the gaps between fibers. On the other hand, when the absorbent sheet 12 is the superabsorbent polymer film, the heat-fusible fibers and the heat-fusible continuous filaments are fusion-bonded to each other via the openings or cuts formed in the film.

As shown in FIGS. 1 and 3, the fixing lines 14 extend in straight in the X direction and are spaced apart from each other in the Y direction by a given pitch. The three-layered structure integrated by forming the fixing lines 14 is then cut into a predetermined length to contain at least two (preferably, four or more) fixing lines 14. Thus, the structural body 10 shown in FIG. 1 is manufactured.

In the structural body 10, since the fibrous absorbent core 11 and the surface layer 13 are fixed at the fixing lines 14 via the through passages of the absorbent sheet 12, the absorbent sheet 12 is certainly and firmly held between the fibrous absorbent core 11 and the surface layer 13. Thus, the fibrous absorbent core 11, the absorbent sheet 12 and the surface layer 13 are so integrated as to prevent displacement relative to each other. Furthermore, since the superabsorbent polymer is in the sheet form, the superabsorbent polymer can be distributed uniformly in the structural body 10. It should be noted that no adhesive is required for integrating the fibrous absorbent core 11, the absorbent sheet 12 and the surface layer 13.

In the sanitary napkin 1 using the structural body 10, menstrual blood applied to the surface layer 13 passes through gaps between continuous filaments to be absorbed in the underlying absorbent sheet 12. As set forth above, since the superabsorbent polymer exists in the form of the absorbent sheet 12, the liquid absorbing performance will never be fluctuated from place to place. Furthermore, since adhesive is not interposed, degradation of liquid permeability of the surface layer 13 and/or liquid absorbing performance of the absorbent sheet 12 will never be caused. Moreover, since the fibrous absorbent core 11 is positioned below the absorbent sheet 12, menstrual blood may also be absorbed by the fibrous absorbent core 11.

In the structural body 10, since the surface layer 13 for directly contacting with the skin of a wearer is formed with continuous filaments, no fiber end appears on the surface thereof. Therefore, the surface layer 13 provides smooth contact feeling to the skin of a wearer. Furthermore, since the continuous filaments are only fixed at the fixing lines, individual filaments may move relatively freely to follow movement of the skin of a wearer. Therefore, it is less irritative to the skin. Also, the surface layer 13 is so bulky to provide superior cushioning ability.

Furthermore, since the continuous filaments of the surface layer 13 extend in the longitudinal direction (Y direction) of the sanitary napkin 1, the liquid is preferentially guided in the longitudinal direction to thereby prevent lateral leakage in the width direction (X direction). Here, since the continuous filaments are fixed at the fixing lines 14 spaced apart in the longitudinal direction by the given pitch, spreading of the liquid in the longitudinal direction in the structural body 10 can be restricted.

FIG. 5 shows a structural body 10A according to another embodiment of the invention, which has the same constructions as those of the structural body 10 shown in FIGS. 1 to 4, except for a pattern of fixing lines. In the structural body 10A shown in FIG. 5, short fixing lines 15 extending in the X direction are arranged in a staggered fashion such that fixing lines in a center row are not continuous to but are offset from fixing lines in each of laterally adjacent rows. In this construction, since there is no fixing line continuously extending across the structural body in the X direction, possibility of causing lateral leakage of menstrual blood along the fixing line can be reduced.

However, fixing lines should not be limited to the foregoing patterns but may extend in various forms, for example, in the form of continuous line approximated to trigonometric curve or V-shaped line. It is also possible to provide a plurality of short fixing lines intermittently arranged at a given interval in the X direction, so long as consideration is given to prevention of falling out of filaments. Various alternation of the short fixing line patterns are disclosed in commonly owned co-pending U.S. patent application, for "ABSORBENT ARTICLE EMPLOYING SURFACE LAYER WITH CONTINUOUS FILAMENT AND MANUFACTURING PROCESS THEREOF" (claiming priority based on Japanese Patent Application No. 2000-265467). The disclosure of the above-identified commonly owned co-pending U. S. patent application will be herein incorporated by reference. Of course, it is possible to replace the short fixing lines with circular dot-shaped fixing portions or the like, for fusion-bonding the surface layer 13 and the fibrous absorbent core 11.

As set forth, the structural body 10 can be manufactured by feeding and stacking the fibrous absorbent core 11, the absorbent sheet 12 and the surface layer 13, and fixing them by the welding roll. Thus, manufacturing process becomes quite simple. Also, since the sanitary napkin 1 can be manufactured with taking the structural body 10, in which a component for directly contacting with the skin of a wearer (i.e., surface layer) and components for absorbing liquid (i.e., absorbent sheet and fibrous absorbent core) are integrated, as primary component, it becomes unnecessary to separately provide a process step for joining a surface sheet (component for directly contacting with the skin of a wearer) onto an absorbent core (component for absorbing liquid) as in the prior art. Therefore, manufacturing process of the sanitary napkin can be simplified.

The continuous filaments forming the surface layer 13 should not be limited to those opened from a tow, but can be spun bonded fibers, melt blown fibers and so forth. In another alternative, the surface layer 13 may be formed of split yarns which are prepared by splitting a film in a width direction to form filaments joined in net form.

The absorbent article according to the present invention is not only applicable for sanitary napkin, but also a panti-liner, disposable diaper and so forth. For instance, the present invention is also applicable for the absorbent articles disclosed in commonly owned co-pending U.S. Patent Application for "ABSORBENT ARTICLE WITH BACKING SHEET HAVING CONTINUOUS FILAMENTS" (claiming priority based on Japanese Patent Application No. 2000-265527) and commonly owned co-pending U.S. Patent Application for "ABSORBENT ARTICLE WITH SURFACE STRUCTURAL BODY OF CONTINUOUS FILAMENTS" (claiming priority based on Japanese Patent Application No. 2000-265519). The disclosures of the above-identified commonly owned co-pending U.S. Patent Applications are herein incorporated by reference.

As set forth, in the present invention, the absorbent sheet formed of superabsorbent polymer can be maintained between the surface layer and the fibrous absorbent core without adhesive, and displacement of the absorbent sheet can be successfully prevented. Therefore, liquid absorbing performance in a liquid absorbing region can be made uniform.

Also, since the surface layer, the fibrous absorbent core and the absorbent sheet can be integrated, it becomes unnecessary to provide a process step for joining a surface sheet on an absorbent core as in the prior art. Therefore, manufacturing process of the absorbent article can be simplified.

The surface layer of the absorbent core has good liquid permeability and can successfully prevent flowing back of the liquid. Furthermore, the surface layer may provide superior cushioning ability to provide soft contact feeling to the skin of a wearer.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. An absorbent article comprising:
   a liquid permeable surface layer formed of continuous filaments individually extending over the entire length of said surface layer, said continuous filaments including at least heat-fusible continuous filaments;
   a backing sheet; and
   a fibrous absorbent core located between said surface layer and said backing sheet and containing heat-fusible fibers,
   wherein between said surface layer and said fibrous absorbent core, disposed is an absorbent sheet which is formed of superabsorbent polymer to have a plurality of through passages, and said surface layer and said fibrous absorbent core are partially fusion-bonded to each other via said through passages formed in said absorbent sheet for retaining said absorbent sheet between said surface layer and said fibrous absorbent core.

2. The absorbent article as set forth in claim 1, wherein said absorbent sheet is formed with superabsorbent polymer fibers, and said surface layer and said fibrous absorbent core are fusion-bonded via gaps defined between fibers of said absorbent sheet.

3. The absorbent article as set forth in claim 1, wherein said absorbent sheet is a superabsorbent polymer film, and said surface layer and said fibrous absorbent core are fusion-bonded via openings or cuts formed in said film.

4. The absorbent article as set forth in claim 1, wherein said heat-fusible continuous filaments in said surface layer and said heat-fusible fibers in said fibrous absorbent core are fusion-bonded at a plurality of fixing lines, which extend in a direction intersecting a direction along which said continuous filaments extend and are spaced apart from each other in the direction along which said continuous filaments extend.

* * * * *